US011384362B1

(12) United States Patent
Padley et al.

(10) Patent No.: US 11,384,362 B1
(45) Date of Patent: Jul. 12, 2022

(54) SQUASH PLANTS WITH RESISTANCE TO DOWNY MILDEW

(71) Applicant: Syngenta Crop Protection AG, Basel (CH)

(72) Inventors: Les Padley, Woodland (CA); Carine Rizzolatti, Saint-Sauveur (FR); Ajay Sandhu, Woodland, CA (US); Kevin L. Cook, New Harbor, ME (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/539,392

(22) Filed: Dec. 1, 2021

(51) Int. Cl.
*C12N 15/82* (2006.01)

(52) U.S. Cl.
CPC ................ *C12N 15/8282* (2013.01)

(58) Field of Classification Search
None
See application file for complete search history.

(56) References Cited

FOREIGN PATENT DOCUMENTS

WO 2022/048726 A1 3/2022

OTHER PUBLICATIONS

Brown and Myers Journal of Amer. Soc. Horti Sci. (2002) 127:568-575.*
Cornell University, College of Agriculture & Life Sciences, Winter Squash Variety-Resistance to Diseases and Physiological Disorders; Updated 2020.
Cornell University, College of Agriculture & Life Sciences, Pumpkin Variety-Resistance to Diseases and Physiological Disorders; Updated 2020.
Cornell University, College of Agriculture & Life Sciences, Zucchini Squash Variety-Resistance to Diseases and Physiological Disorders; Updated 2020.
Newark et al., "Management of Cucurbit Downy Mildew in Florida", University of Florida, IFAS Extension, (2019) pp. 325; 1-6.
Edmund Frost, "Identifying and Marketing Quality Open-Pollinated and Organic Cucurbit Seedstocks for Virginia", University of Maryland, 2021 Sustainable Agriculture Research & Education.
Montero-Pau et al, "De novo assembly of the zucchini genome reveals a whole-genome duplication associated with the origin of the *Cucurbita* genus," Plant Biotechnology Journal (2018) 16, pp. 1161-1171.

* cited by examiner

*Primary Examiner* — Medina A Ibrahim
(74) *Attorney, Agent, or Firm* — Karen A. Magri

(57) ABSTRACT

The present invention relates to novel squash plants displaying an increased resistance to downy mildew infection. The present invention also relates to seeds and parts of said plants, for example fruits. The present invention further relates to methods of making and using such seeds and plants. The present invention also relates to novel genetic sequences associated with said increased resistance and to molecular markers associated with said novel genetic sequences.

18 Claims, 2 Drawing Sheets

Specification includes a Sequence Listing.

(a)

(b)

(c)

(d)

(e)

(a)

(b)

SEQUENCE LISTING

```
<160> NUMBER OF SEQ ID NOS: 8

<210> SEQ ID NO 1
<211> LENGTH: 71
<212> TYPE: DNA
<213> ORGANISM: Cucurbita pepo

<400> SEQUENCE: 1
tccacagcag ctctcgctgc agctgctgca taagcggcag actcgaatgc tgcctgagct    60
gcatcggcca c                                                         71

<210> SEQ ID NO 2
<211> LENGTH: 71
<212> TYPE: DNA
<213> ORGANISM: Cucurbita pepo

<400> SEQUENCE: 2
ctgaactaac atctgcaatt ttcaataaag taatcgagaa ctaccttgaa ggaagtggtt    60
gaatgaggaa g                                                         71

<210> SEQ ID NO 3
<211> LENGTH: 71
<212> TYPE: DNA
<213> ORGANISM: Cucurbita pepo
<220> FEATURE:
<221> NAME/KEY: misc_feature
<222> LOCATION: (37)..(38)
<223> OTHER INFORMATION: n is a, c, g, or t

<400> SEQUENCE: 3
gaccgttgac atgcatgtat gattatggta ttattgnntg tttttttaa ggtctaattg     60 ttgtgttttt t                                                         71

<210> SEQ ID NO 4
<211> LENGTH: 71
<212> TYPE: DNA
<213> ORGANISM: Cucurbita pepo

<400> SEQUENCE: 4
gtgatttgag gagggattct ttccatttga atcrtaatga tgaccaggag agtctgaaga    60
```

-continued

```
tggttgcaac g                                                          71

<210> SEQ ID NO 5
<211> LENGTH: 71
<212> TYPE: DNA
<213> ORGANISM: Cucurbita pepo

<400> SEQUENCE: 5
gctaaagcta cgcaatcgga ttgaatccca gcaggatcca caacaaacaa tcaaayarca    60
atagaatccg a                                                         71

<210> SEQ ID NO 6
<211> LENGTH: 71
<212> TYPE: DNA
<213> ORGANISM: Cucurbita pepo

<400> SEQUENCE: 6
agtatgtttc ttccaccacg accaacaact aacccgatgt ggccatckga aacrccaatg    60
gtcaaagagt t                                                         71

<210> SEQ ID NO 7
<211> LENGTH: 71
<212> TYPE: DNA
<213> ORGANISM: Cucurbita pepo

<400> SEQUENCE: 7
agttcraaga gttagggtta cgatttcttc ggaagggrga ratataaaat aatctccaaa    60
acgagctgga a                                                         71

<210> SEQ ID NO 8
<211> LENGTH: 71
<212> TYPE: DNA
<213> ORGANISM: Cucurbita pepo

<400> SEQUENCE: 8
gagtggtggg gagggctacy tacttaggwt gttacatgag atgatgatgg aattgatgaa    60
gaagctattt g                                                         71
```

SQUASH PLANTS WITH RESISTANCE TO DOWNY MILDEW

FIELD OF THE INVENTION

The present invention relates to novel squash plants displaying an increased resistance to downy mildew infection. The present invention also relates to seeds and parts of said plants, for example fruits. The present invention further relates to methods of making and using such seeds and plants. The present invention also relates to novel genetic sequences associated with said increased resistance and to molecular markers associated with said novel genetic sequences.

BACKGROUND OF THE INVENTION

Squash [*Cucurbita pepo* L.] is an important specialty crop native of North America. The cultivated, edible forms of *Cucurbita* are a common crop in many major agriculture production areas and represented a world production of 22,900,826 tonnes in 2019 (derived from data supplied by the Food and Agriculture Organization). The United States production alone was worth up to 220 million of US dollars in 2019 (USDA Vegetables 2019 Summary).

Plant pathogens are known to cause massive damage to important crops, including squash, resulting in significant agricultural losses with widespread consequences for both the food supply and other industries that rely on plant materials. As such, there is a long felt need to reduce the incidence and/or impact of agricultural pests on crop production. An example of such pathogens is *Pseudoperonospora cubensis* (*P. cubensis*), an obligate biotrophic agent responsible for the downy mildew disease. Downy mildew is known to devastate various Cucurbitaceae crop plants including, but not limited to cucumber, squash, melon and watermelon.

While a few winter squash accessions [*Cucurbita moschata* L] were reported to be downy mildew resistant (Frost, 2015), to our knowledge, there are currently no downy mildew tolerant or resistant commercial *C. pepo* material with acceptable horticultural quality (producing sweet, edible fruits) available to squash growers. One of the latest reports on the management of downy mildew for cucurbits crops does not reference tolerant or resistant squash varieties (Newark et al. 2019, table 2). Therefore, there remains a need for novel sources of resistance against downy mildew strains, which would provide for easier and better downy mildew resistance management while being adaptable into commercially relevant squash germplasm.

SUMMARY OF THE INVENTION

The present invention addresses the need for an improved resistance to downy mildew by providing novel squash plants comprising an increased downy mildew resistance trait. By identifying one QTL associated with increased downy mildew resistance in a breeding population and by introgressing its corresponding sequence into elite squash plants, the downy mildew resistance capability of the squash plant was increased, which has a positive impact on overall plant performance. The downy mildew resistance QTL and its corresponding introgressed sequence, located on chromosome 9 (QTL9), is of semi-dominant nature, hence one copy of the sequence is sufficient to provide an improved downy mildew resistance phenotype.

Altogether, the characteristics of the improved downy mildew resistant squash plant disclosed within the present invention provide a squash grower with novel solutions to enhance economic and commercial efficiency when deploying squash varieties in a downy mildew pressured field.

In a first embodiment, the invention provides a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant resistant to downy mildew infection, comprising in its genome an introgressed sequence from *Cucurbita pepo* subsp. *ovifera* var. *recticollis* plant which confers resistance to downy mildew, wherein said introgressed sequence is located on chromosome 9 and comprises at least one of the following SNP markers:

a) a G genotype in the heterozygous or homozygous state for SNP marker 1 at a position corresponding to position 36 in SEQ ID NO: 1;
b) a G genotype in the heterozygous or homozygous state for SNP marker 2 at a position corresponding to position 36 in SEQ ID NO: 2;
c) a G genotype in the heterozygous or homozygous state for SNP marker 3 at a position corresponding to position 36 in SEQ ID NO: 3;
d) an A genotype in the heterozygous or homozygous state for SNP marker 4 at a position corresponding to position 36 in SEQ ID NO: 4;
e) an A genotype in the heterozygous or homozygous state for SNP marker 5 at a position corresponding to position 36 in SEQ ID NO: 5;
f) an A genotype in the heterozygous or homozygous state for SNP marker 6 at a position corresponding to position 36 in SEQ ID NO: 6;
g) an A genotype in the heterozygous or homozygous state for SNP marker 7 at a position corresponding to position 36 in SEQ ID NO: 7; and/or,
h) an A genotype in the heterozygous or homozygous state for SNP marker 8 at a position corresponding to position 36 in SEQ ID NO: 8.

In a further embodiment of the invention, said downy mildew resistance-conferring introgressed sequence comprises at least one of SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8, or a sequence that is at least 80%, preferably at least 85%, more preferably at least 90%, even more preferably at least 95% identical to one or more of said sequences.

In a further embodiment of the invention, said plant is heterozygous for said at least one SNP marker. In a further embodiment of the invention, said plant is homozygous for said at least one SNP marker.

In a further embodiment of the invention, said introgressed sequence is comprised in *Cucurbita pepo* plant 21SQN100201, representative seed of which is deposited under ATCC Accession No. PTA-127157, or a progeny or an ancestor thereof.

In a further embodiment, the invention provides a plant according to any of the preceding embodiments wherein said plant is obtained by crossing *Cucurbita pepo* plant 21SQN100201, representative seed of which is deposited under ATCC Accession No. PTA-127157, or a progeny or an ancestor thereof, with a squash plant that does not contain said downy mildew resistance-conferring introgressed sequence.

In a further embodiment, the invention provides a plant according to any of the preceding embodiments, wherein said plant is an inbred, a dihaploid, a diploid, or a hybrid plant.

It is a further embodiment to provide a plant part, organ or tissue obtainable from a squash plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the downy mildew resistance trait according to the invention, particularly when grown into a plant that produces fruits.

In a further embodiment, the invention provides a seed that produces a plant according to any of the preceding embodiments.

In a further embodiment, the invention provides a method for producing a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant resistant to downy mildew infection comprising the steps of
  a) crossing a plant according to any one of the preceding embodiments with a cultivated squash plant lacking said downy mildew resistance-conferring introgressed sequence;
  b) selecting a progeny plant comprising said introgressed sequence located on chromosome 9 conferring resistance to downy mildew, said selecting step comprising detecting at least one of the following SNP markers:
    i) a G genotype in the heterozygous or homozygous state for SNP marker 1 at a position corresponding to position 36 in SEQ ID NO: 1;
    ii) a G genotype in the heterozygous or homozygous state for SNP marker 2 at a position corresponding to position 36 in SEQ ID NO: 2;
    iii) a G genotype in the heterozygous or homozygous state for SNP marker 3 at a position corresponding to position 36 in SEQ ID NO: 3;
    iv) an A genotype in the heterozygous or homozygous state for SNP marker 4 at a position corresponding to position 36 in SEQ ID NO: 4;
    v) an A genotype in the heterozygous or homozygous state for SNP marker 5 at a position corresponding to position 36 in SEQ ID NO: 5;
    vi) an A genotype in the heterozygous or homozygous state for SNP marker 6 at a position corresponding to position 36 in SEQ ID NO: 6;
    vii) an A genotype in the heterozygous or homozygous state for SNP marker 7 at a position corresponding to position 36 in SEQ ID NO: 7; and/or,
    viii) an A genotype in the heterozygous or homozygous state for SNP marker 8 at a position corresponding to position 36 in SEQ ID NO: 8;
thereby producing a plant with enhanced resistance to downy mildew. In a further embodiment, the invention relates to the method of any of the preceding embodiments, wherein the method further comprises:
  c) selfing the selected progeny or crossing the selected progeny with another squash plant to produce further progeny.

In a further embodiment, the invention relates to the method of the preceding embodiment, wherein further progeny is selected and selfed/crossed for 2 to 10 more generations.

In a further embodiment, the invention relates to the method of any of the preceding embodiments, wherein the plant of step a) is *Cucurbita pepo* plant 21SQN100201, representative seed of which is deposited under ATCC Accession No. PTA-127157, or a progeny or an ancestor thereof.

In a further embodiment, the invention relates to a method for producing a F1 squash plant exhibiting resistance to downy mildew, the method comprising crossing an inbred squash plant, which is a plant according to any one of the preceding embodiments, with a different inbred squash plant to produce F1 hybrid progeny.

In a further embodiment, the invention provides a method for identifying a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant, exhibiting resistance to downy mildew and having at least one copy of said downy mildew resistance-conferring introgressed sequence, said method comprising the step of detecting at least one of the following SNP markers:
  a) a G genotype in the heterozygous or homozygous state for SNP marker 1 at a position corresponding to position 36 in SEQ ID NO: 1;
  b) a G genotype in the heterozygous or homozygous state for SNP marker 2 at a position corresponding to position 36 in SEQ ID NO: 2;
  c) a G genotype in the heterozygous or homozygous state for SNP marker 3 at a position corresponding to position 36 in SEQ ID NO: 3;
  d) an A genotype in the heterozygous or homozygous state for SNP marker 4 at a position corresponding to position 36 in SEQ ID NO: 4;
  e) an A genotype in the heterozygous or homozygous state for SNP marker 5 at a position corresponding to position 36 in SEQ ID NO: 5;
  f) an A genotype in the heterozygous or homozygous state for SNP marker 6 at a position corresponding to position 36 in SEQ ID NO: 6;
  g) an A genotype in the heterozygous or homozygous state for SNP marker 7 at a position corresponding to position 36 in SEQ ID NO: 7; and/or,
  h) an A genotype in the heterozygous or homozygous state for SNP marker 8 at a position corresponding to position 36 in SEQ ID NO: 8;
thereby identifying a squash plant exhibiting resistance to downy mildew.

In a further embodiment, the invention relates to the method of the preceding embodiment, wherein said method further comprises selecting a squash plant comprising said one or more SNP markers, and crossing the selected squash plant with a second squash plant to produce progeny squash plants that comprise at least one of said SNP markers and exhibits increased resistance to downy mildew.

DETAILED DESCRIPTION OF THE INVENTION

Definitions

Figure 1:
FIG. 1 shows downy mildew pathology assay pictures representative of the disease scale used and described in Example 2C. (a) Rating 1; (b) Rating 3; (c) Rating 5; (d) Rating 7; (e) Rating 9.
Figure 1:
Figure 1:
Figure 1:
Figure 1:

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "cultivated squash" or an "elite squash" plant is understood within the scope of the invention to refer to a plant that is no longer in the natural state but has been developed and domesticated by human care and for agricultural use and/or human consumption, and excludes wild squash accessions, such as *C. pepo* subsp. *moschata* accessions. As a matter of example, in embodiments, a cultivated or elite squash plant according to the present invention is capable of growing edible, palatable fruits. Alternatively, or additionally, the cultivated squash plant is a hybrid plant. Alternatively, or additionally, the cultivated squash plant is a *C. pepo* subsp. *pepo* var. *cylindrica*, a *C. pepo* subsp. *pepo* var. ionga, a *C. pepo* subsp. *pepo* var. *pepo*, a *C. pepo* subsp. *ovifera* var. *recticollis*, a *C. pepo* subsp. *ovifera* var. torticollia, or a *C. pepo* subsp. *ovifera* var. *clypeata*, preferably a *C. pepo* subsp. *pepo* var. *cylindrica* plant, more preferably a cultivated zucchini squash plant.

An "allele" is understood within the scope of the invention to refer to alternative or variant forms of various genetic units identical or associated with different forms of a gene or of any kind of identifiable genetic determinant such as a QTL, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, chemical or structural modification, transcription regulation or post-translational modification/regulation. In a diploid cell or organism, the two alleles of a given gene or genetic element typically occupy corresponding loci on a pair of homologous chromosomes.

Relatively speaking, the term "improved downy mildew resistance" or "increased downy mildew resistance" is herein understood to mean that a plant according to the present invention, e.g. comprising an introgressed sequence from *Cucurbita pepo* subsp. *ovifera* var. *recticollis* plant which confers resistance to downy mildew, wherein said introgressed sequence is located on chromosome 9 and comprises at least one of SNP markers 1 to 8, is more tolerant or more resistant to downy mildew when compared with a plant lacking said introgressed sequence.

"Improved downy mildew resistance" is understood within the scope of the invention to mean a squash plant which has a statistically significant improved resistance to downy mildew compared to a control squash plant lacking the introgressed sequence of the invention (for example as described in the Example section), using standard error and/or at $P<0.05$ or $P<0.01$ using Student's test.

"Phenotype" is understood within the scope of the invention to refer to a distinguishable characteristic(s) of a genetically controlled trait.

A "control squash plant" is understood within the scope of the invention to mean a squash plant that has the same genetic background as the cultivated squash plant of the present invention wherein the control plant does not have the introgressed sequence of the present invention linked to improved downy mildew resistance. In particular a control squash plant is a squash plant belonging to the same plant variety and does not comprise the introgressed sequence of the present invention. The control squash plant is grown for the same length of time and under the same conditions as the cultivated squash plant of the present invention. Plant variety is herein understood according to definition of UPOV. Thus, a control squash plant may be a near-isogenic line, an inbred line or a hybrid provided that they have the same genetic background as the squash plant of the present invention except the control plant does not have the introgressed sequence of the present invention linked to improved downy mildew resistance.

The term "trait" refers to a characteristic or a phenotype. In the context of the present invention, a downy mildew resistance trait is an improved downy mildew resistance trait. A trait may be inherited in a dominant or recessive manner, or in a partial, semi- or incomplete-dominant manner. In the context of the present invention, the downy mildew resistance-conferring introgressed sequence located on chromosome 9 is semi-dominant.

A squash plant of the invention can therefore be heterozygous or homozygous for the trait. Furthermore, a trait may be monogenic or polygenic, or may result from the interaction of one or more genes with the environment. In the context of the present invention, the downy mildew resistance-conferring introgressed sequence located on chromosome 9 is sufficient to confer, alone, the improved downy mildew resistance trait.

The terms "hybrid", "hybrid plant", and "hybrid progeny" refer to an individual produced from genetically different parents (e.g., a genetically heterozygous or mostly heterozygous individual).

The term "inbred line" refers to a genetically homozygous or nearly homozygous population. An inbred line, for example, can be derived through several cycles of brother/sister breeding or of selfing or in dihaploid production.

The term "dihaploid line" refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets is named "dihaploid" and are essentially no longer segregating (stable).

The term "genetically fixed" refers to a genetic sequence which has been stably incorporated into the genome of a plant that normally does not contain said genetic sequence. When genetically fixed, the genetic sequence can be transmitted in an easy and predictable manner to other plants by sexual crosses.

The term "rootstock" refers to a plant used as a receptacle for a scion plant. Typically, the rootstock plant and the scion plant are of different genotypes. In embodiments, plants according to the present invention are used as rootstock plants.

The term "plant" or "plant part' refers hereinafter to a plant part, organ or tissue obtainable from a squash plant according to the invention, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the improved downy mildew resistance trait according to the invention, particularly when grown into a plant that produces fruits.

A "plant" is any plant at any stage of development.

A squash plant seed is a seed which grows into a squash plant according to any of the embodiments.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes. In the context of the invention, a squash plant comprising two identical copies of a particular introgressed sequence at a particular locus, e.g., the introgressed sequence located on chromosome 9, is homozygous on a corresponding locus.

"Heterozygous" is understood within the scope of the invention to refer to unlike alleles at one or more corresponding loci on homologous chromosomes. In the context of the invention, a squash plant comprising one copy of a particular introgressed sequence at a particular locus, e.g., the introgressed sequence located on chromosome 9, is heterozygous on a corresponding locus.

A "dominant" allele is understood within the scope of the invention to refer to an allele which determines the phenotype when present in the heterozygous or homozygous state.

A "semi-dominant" allele is understood within the scope of the invention to refer to an allele which determines the phenotype when present in the heterozygous or homozygous state. The intensity of the phenotype is however generally higher when the allele is present in the homozygous state.

A "recessive" allele refers to an allele which determines the phenotype when present in the homozygous state only.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene, a QTL or its corresponding genetic sequence contributing to a trait.

As used herein, "marker locus" refers to a region on a chromosome, which comprises a nucleotide or a polynucleotide sequence that is present in an individual's genome and that is associated with one or more loci of interest, which may comprise a gene or any other genetic determinant or factor contributing to a trait.

"Genetic linkage" is understood within the scope of the invention to refer to an association of characters in inheritance due to location of genes in proximity on the same chromosome, measured by percent recombination between loci (centi-Morgan, cM).

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" refers to, in some embodiments, fertilization of one individual by another (e.g., cross-pollination in plants). The term "selfing" refers, in some embodiments, to the production of seed by self-fertilization or self-pollination, i.e., pollen and ovule are from the same plant.

As used herein, the phrase "genetic marker" or "DNA marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

As used herein, the term "genotype" refers to the genetic constitution of a cell or organism. An individual's "genotype for a set of genetic markers" includes the specific alleles, for one or more genetic marker loci, present in the individual's haplotype.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the terms "quantitative trait locus" (QTL) refer to an association between a genetic marker and a chromosomal region and/or gene and/or introgressed sequence that affects the phenotype of a trait of interest. Typically, this is determined statistically, e.g., based on one or more methods published in the literature. A QTL can be a chromosomal region and/or a genetic locus with at least two alleles that differentially affect a phenotypic trait.

The term "recipient squash plant" is used herein to indicate a squash plant that is to receive DNA obtained from a donor squash plant that comprises an introgressed sequence for improved downy mildew resistance.

The term "natural genetic background" is used herein to indicate the original genetic background of genetic sequence. For instance, the genetic sequence of the present invention was found at a specific location on chromosome 9 of a *Cucurbita pepo* subsp. *ovifera* var. *recticollis* plant. Conversely, a method that involves the transfer of DNA, via e.g., breeding, comprising this genetic sequence from chromosome 9 of *Cucurbita pepo* subsp. *ovifera* var. *recticollis* plant to the same position on chromosome 9 of another squash species, preferably a cultivated squash plant, even more preferably a *C. pepo* subsp. *pepo* var. *cylindrica* plant, will result in this genetic sequence not being in its natural genetic background. When the genetic sequence of the present invention is transferred from a *Cucurbita pepo* subsp. *ovifera* var. *recticollis* background into another squash species, preferably a cultivated squash plant, even more preferably a *C. pepo* subsp. *pepo* var. *cylindrica* plant, they are referred to as "introgressed sequence" or "introgressed genetic sequence".

A "donor squash plant" is understood within the scope of the invention to mean the squash plant which provides the introgressed sequence for improved downy mildew resistance.

"Marker-based selection" is understood within the scope of the invention to refer to e.g. the use of genetic markers to detect one or more nucleic acids from the plant, where the nucleic acid is associated with a desired trait to identify plants that carry alleles for desirable (or undesirable) traits, so that those plants can be used (or avoided) in a selective breeding program.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (i.e., amplified sequence or target), one or more labelled allele-specific oligonucleotide probes and a detection system that records and interprets the hybridization signal. The presence or absence of the desired SNP marker allele may be determined by real-time PCR using double-stranded DNA dyes or the fluorescent reporter probe method.

"PCR (Polymerase chain reaction)" is understood within the scope of the invention to refer to a method of producing relatively large amounts of specific regions of DNA or subset(s) of the genome, thereby making possible various analyses that are based on those regions. "PCR primer" is understood within the scope of the invention to refer to relatively short fragments of single-stranded DNA used in the PCR amplification of specific regions of DNA.

"Probe" as used herein refers to a group of atoms or molecules which can recognise and bind to a specific target molecule or cellular structure and thus allowing detection of the target molecule or structure. Particularly, "probe" refers to a labelled DNA or RNA sequence which can be used to detect the presence of and to quantitate a complementary sequence by molecular hybridization.

"Sequence Identity". The terms "identical" or "identity" in the context of two or more nucleic acid or protein sequences, refer to two or more sequences or sub-sequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequence of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

EMBODIMENTS

Plants, Seeds, Fruits.

In a first embodiment, the invention provides a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant resistant to downy mildew infection, comprising in its genome an introgressed sequence from *Cucurbita pepo* subsp. *ovifera* var. *recticollis* which confers resistance to downy mildew, wherein said introgressed sequence is located on chromosome 9 and comprises at least one of the following SNP markers:
- a) a G genotype in the heterozygous or homozygous state for SNP marker 1 at a position corresponding to position 36 in SEQ ID NO: 1;
- b) a G genotype in the heterozygous or homozygous state for SNP marker 2 at a position corresponding to position 36 in SEQ ID NO: 2;
- c) a G genotype in the heterozygous or homozygous state for SNP marker 3 at a position corresponding to position 36 in SEQ ID NO: 3;
- d) an A genotype in the heterozygous or homozygous state for SNP marker 4 at a position corresponding to position 36 in SEQ ID NO: 4;
- e) an A genotype in the heterozygous or homozygous state for SNP marker 5 at a position corresponding to position 36 in SEQ ID NO: 5;
- f) an A genotype in the heterozygous or homozygous state for SNP marker 6 at a position corresponding to position 36 in SEQ ID NO: 6;
- g) an A genotype in the heterozygous or homozygous state for SNP marker 7 at a position corresponding to position 36 in SEQ ID NO: 7; and/or,
- h) an A genotype in the heterozygous or homozygous state for SNP marker 8 at a position corresponding to position 36 in SEQ ID NO: 8.

In a further embodiment of the invention, said downy mildew resistance-conferring introgressed sequence comprises at least one of SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8, or a sequence that is at least 80%, preferably at least 85%, more preferably at least 90%, even more preferably at least 95% identical to one or more of said sequences.

In a further embodiment of the invention, said plant comprises SNP marker 3.

In a further embodiment of the invention, said plant is heterozygous for said at least one SNP marker. In a further embodiment of the invention, said plant is homozygous for said at least one SNP marker.

In a further embodiment of the invention, said introgressed sequence is comprised in *Cucurbita pepo* plant 21SQN100201, representative seed of which is deposited under ATCC Accession No. PTA-127157, or a progeny or an ancestor thereof.

In a further embodiment, the invention provides a plant according to any of the preceding embodiments wherein said plant is obtained by crossing *Cucurbita pepo* plant 21SQN100201, representative seed of which is deposited under ATCC Accession No. PTA-127157, or a progeny or an ancestor thereof, with a squash plant that does not contain said downy mildew resistance-conferring introgressed sequence. In a further embodiment, the invention provides a plant according to any of the preceding embodiments, wherein said plant is an inbred, a dihaploid, a diploid, or a hybrid plant.

In another embodiment, the plant according to the invention is male sterile. In another embodiment, the plant according to the invention is cytoplasmic male sterile.

In a further embodiment, the squash plant of the invention is a squash plant according to any of preceding embodiments, wherein said downy mildew resistance-conferring introgressed sequence located on chromosome 9 can be identified using any of the SNP markers 1 to 8 disclosed in Table 4 hereinbelow.

In a further embodiment, the invention provides a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant resistant to downy mildew infection, comprising in its genome an introgressed sequence from *Cucurbita pepo* subsp. *ovifera* var. *recticollis* which confers resistance to downy mildew located on chromosome 9, wherein said plant genome comprises:
- a) a G genotype in the heterozygous or homozygous state for SNP marker 1 at a position corresponding to position 36 in SEQ ID NO: 1, and
- b) an A genotype in the heterozygous or homozygous state for SNP marker 8 at a position corresponding to position 36 in SEQ ID NO: 8.

In a further embodiment, the cultivated squash plant of the previous embodiment further comprises at least a third resistant allele at any of the SNP markers 2 to 7 disclosed in Table 4.

In a further embodiment, the invention provides a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant resistant to downy mildew infection, comprising in its genome an introgressed sequence from *Cucurbita pepo* subsp. *ovifera* var. *recticollis* which confers resistance to downy mildew located on chromosome 9, wherein said plant genome comprises:
- a) a G genotype in the heterozygous or homozygous state for SNP marker 3 at a position corresponding to position 36 in SEQ ID NO: 3.

In a further embodiment, the squash plant of the invention is a squash plant according to any of the preceding embodiments, wherein *Cucurbita pepo* plant 21SQN100201, representative seed of which is deposited under ATCC Accession No. PTA-127157, or a progeny or an ancestor thereof, is the source of said downy mildew resistance-conferring introgressed sequence.

It is a further embodiment to provide a plant part, organ or tissue obtainable from a squash plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the downy mildew resistance trait according to the invention, particularly when grown into a plant that produces fruits.

In a further embodiment, the invention provides a seed that produces a plant according to any of the preceding embodiments.

In a further embodiment the invention relates to the use of a squash plant according to any of the preceding embodiments as a rootstock, preferably a cucurbit rootstock, more preferably a squash rootstock. In a further embodiment the invention relates to the use of *Cucurbita pepo* plant 21SQN100201, representative seed of which is deposited under ATCC Accession No. PTA-127157, or a progeny or an ancestor thereof, as a squash rootstock.

In another embodiment is considered the use of a squash plant, plant part or seed according to any of the preceding embodiments for producing and harvesting squash fruits.

In another embodiment the invention relates to the use of a squash plant, plant part or seed according to any embodiments, wherein the squash plant, plant part or seed is *Cucurbita pepo* plant 21SQN100201, representative seed of which is deposited under ATCC Accession No. PTA-127157, or a progeny or an ancestor thereof.

In a further embodiment the invention relates to the use of a squash plant, plant part or seed according to any of the preceding embodiments to sow a field, a greenhouse, or a plastic house.

In one embodiment, the invention provides squash fruits produced by a squash plant according to any of the preceding embodiments.

The invention further relates to the use of a squash plant according to any of the preceding embodiments to introgress a downy mildew resistance trait into a squash plant lacking said downy mildew resistance trait.

Genetic Sequences, Markers.

The present invention is further directed to an introgressed genetic sequence linked to the downy mildew resistance trait in the squash plant. In a further embodiment, the genetic sequence of the present invention is located on chromosome 9. In a further embodiment of the present invention, the genetic sequence is comprised in, obtained from or obtainable from a donor plant of *Cucurbita pepo* plant 21SQN100201, representative seed of which is deposited under ATCC Accession No. PTA-127157, or a progeny or an ancestor thereof, and comprising said genetic sequence.

In another embodiment, the introgressed genetic sequence of the present invention is located on chromosome 9 and is characterized by at least one of the following SNP markers:
 a) a G genotype in the heterozygous or homozygous state for SNP marker 1 at a position corresponding to position 36 in SEQ ID NO: 1;
 b) a G genotype in the heterozygous or homozygous state for SNP marker 2 at a position corresponding to position 36 in SEQ ID NO: 2;
 c) a G genotype in the heterozygous or homozygous state for SNP marker 3 at a position corresponding to position 36 in SEQ ID NO: 3;
 d) an A genotype in the heterozygous or homozygous state for SNP marker 4 at a position corresponding to position 36 in SEQ ID NO: 4;
 e) an A genotype in the heterozygous or homozygous state for SNP marker 5 at a position corresponding to position 36 in SEQ ID NO: 5;
 f) an A genotype in the heterozygous or homozygous state for SNP marker 6 at a position corresponding to position 36 in SEQ ID NO: 6;
 g) an A genotype in the heterozygous or homozygous state for SNP marker 7 at a position corresponding to position 36 in SEQ ID NO: 7; and/or,
 h) an A genotype in the heterozygous or homozygous state for SNP marker 8 at a position corresponding to position 36 in SEQ ID NO: 8.

The present invention also discloses the use of at least one, at least two or at least three of the SNP markers according to the invention for diagnostic selection and/or genotyping of the downy mildew resistance trait locus in a squash plant, particularly a cultivated squash plant.

The present invention further discloses the use of at least one, at least two or at least three of the SNP markers according to the invention for identifying in a squash plant, particularly a cultivated squash plant, more particularly a squash plant according to the invention, the presence of the downy mildew resistance trait and/or for monitoring the introgression of the downy mildew resistance trait in a squash plant, particularly a cultivated squash plant, particularly a squash plant according to the invention and as described herein.

The present invention therefore further relates in one embodiment to derived markers, particularly to derived primers or probes, developed from an amplification product according to the invention and as described herein above by methods known in the art, which derived markers are genetically linked to the downy mildew resistance trait locus.

Methods of Breeding.

In a further embodiment, the invention provides a method for producing a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant resistant to downy mildew infection comprising the steps of
 a) crossing a plant according to any one of the preceding embodiments with a cultivated squash plant lacking said downy mildew resistance-conferring introgressed sequence;
 b) selecting a progeny plant comprising said introgressed sequence located on chromosome 9 conferring resistance to downy mildew, said selecting step comprising detecting at least one of the following SNP markers:
  i) a G genotype in the heterozygous or homozygous state for SNP marker 1 at a position corresponding to position 36 in SEQ ID NO: 1;
  ii) a G genotype in the heterozygous or homozygous state for SNP marker 2 at a position corresponding to position 36 in SEQ ID NO: 2;
  iii) a G genotype in the heterozygous or homozygous state for SNP marker 3 at a position corresponding to position 36 in SEQ ID NO: 3;
  iv) an A genotype in the heterozygous or homozygous state for SNP marker 4 at a position corresponding to position 36 in SEQ ID NO: 4;
  v) an A genotype in the heterozygous or homozygous state for SNP marker 5 at a position corresponding to position 36 in SEQ ID NO: 5;
  vi) an A genotype in the heterozygous or homozygous state for SNP marker 6 at a position corresponding to position 36 in SEQ ID NO: 6;
  vii) an A genotype in the heterozygous or homozygous state for SNP marker 7 at a position corresponding to position 36 in SEQ ID NO: 7; and/or,
  viii) an A genotype in the heterozygous or homozygous state for SNP marker 8 at a position corresponding to position 36 in SEQ ID NO: 8;
thereby producing a plant with enhanced resistance to downy mildew.

In a further embodiment, the invention relates to the method of any of the preceding embodiments, wherein the method further comprises:
 c) selfing the selected progeny or crossing the selected progeny with another squash plant to produce further progeny.

In a further embodiment, the invention relates to the method of the preceding embodiment, wherein further progeny is selected and selfed/crossed for 2 to 10 more generations.

In a further embodiment, the invention relates to the method of any of the preceding embodiments, wherein the plant of step a) is *Cucurbita pepo* plant 21SQN100201, representative seed of which is deposited under ATCC Accession No. PTA-127157, or a progeny or an ancestor thereof.

In another embodiment the invention relates to a method of providing a downy mildew resistant squash plant, plant part or seed, wherein said method comprises the following steps:
  a) Crossing a 1$^{st}$ plant lacking the downy mildew resistance-conferring introgressed sequence of the invention with a 2$^{nd}$ squash plant according to any embodiments,
  b) Obtaining a progeny squash plant, and,
  c) Optionally, selecting a plant of said progeny characterized in that said plant exhibits resistance to downy mildew.

In a further embodiment the invention relates to the method of the preceding embodiment wherein the 2$^{nd}$ squash plant is *Cucurbita pepo* plant 21SQN100201, representative seed of which is deposited under ATCC Accession No. PTA-127157, or a progeny or an ancestor thereof.

In another embodiment the invention relates to a method for producing a downy mildew resistant squash plant comprising the following steps:
  a) Providing seeds of a squash plant according to any of the preceding embodiments,
  b) Germinating said seed and growing a mature, fertile plant therefrom,
  c) Inducing self-pollination of said plant under a), growing fruits and harvesting the fertile seeds therefrom, and
  d) Growing plants from the seeds harvested under c) and selecting a downy mildew resistant squash plant.

In another embodiment the invention relates to a method for increasing the resistance to downy mildew of a squash plant, comprising the steps of:
  a) selecting a squash, which comprises a downy mildew resistance trait associated with one introgressed sequence located on chromosome 9, wherein said trait can be identified by the presence of at least one of the SNP markers listed in Table 4;
  b) crossing said plant of step a), which comprises a downy mildew resistance trait, with a squash plant, particularly a cultivated squash plant, which does not comprise a downy mildew resistance trait and shows susceptibility to downy mildew, as compared to the plant of step a), and
  c) selecting progeny from said cross which shows increased downy mildew resistance, as compared to the plant of step b).

In a further embodiment, the invention relates to a method for producing a F1 squash plant exhibiting resistance to D downy mildew M, the method comprising crossing an inbred squash plant, which is a plant according to any one of the preceding embodiments, with a different inbred squash plant to produce F1 hybrid progeny.

Methods of Selection.

In a further embodiment, the invention provides a method for identifying a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant, exhibiting resistance to downy mildew and having at least one copy of said downy mildew resistance-conferring introgressed sequence, said method comprising the step of detecting at least one of the following SNP markers:
  a) a G genotype in the heterozygous or homozygous state for SNP marker 1 at a position corresponding to position 36 in SEQ ID NO: 1;
  b) a G genotype in the heterozygous or homozygous state for SNP marker 2 at a position corresponding to position 36 in SEQ ID NO: 2;
  c) a G genotype in the heterozygous or homozygous state for SNP marker 3 at a position corresponding to position 36 in SEQ ID NO: 3;
  d) an A genotype in the heterozygous or homozygous state for SNP marker 4 at a position corresponding to position 36 in SEQ ID NO: 4;
  e) an A genotype in the heterozygous or homozygous state for SNP marker 5 at a position corresponding to position 36 in SEQ ID NO: 5;
  f) an A genotype in the heterozygous or homozygous state for SNP marker 6 at a position corresponding to position 36 in SEQ ID NO: 6;
  g) an A genotype in the heterozygous or homozygous state for SNP marker 7 at a position corresponding to position 36 in SEQ ID NO: 7; and/or,
  h) an A genotype in the heterozygous or homozygous state for SNP marker 8 at a position corresponding to position 36 in SEQ ID NO: 8;
thereby identifying a squash plant exhibiting resistance to downy mildew.

In a further embodiment, the invention relates to the method of the preceding embodiment, wherein said method further comprises selecting a squash plant comprising said one or more SNP markers, and crossing the selected squash plant with a second squash plant to produce progeny squash plants that comprise at least one of said SNP markers and exhibits resistance to downy mildew.

In another embodiment the invention relates to a method of identifying a squash plant comprising the downy mildew resistance-conferring introgressed sequence of the invention, wherein said method comprises the steps of:
  a) providing a population segregating for the downy mildew resistance trait,
  b) screening the segregating population for a member exhibiting resistance to downy mildew, wherein said trait can be identified by the presence of downy mildew resistance-conferring introgressed sequence of the invention,
  c) selecting one member of the segregating population, wherein said member comprises the downy mildew resistance trait.

In a further embodiment, the invention provides a method for identifying a cultivated squash plant comprising an introgressed sequence on chromosome 9, wherein said introgressed sequence confers resistance to downy mildew, comprising:
  a) providing a population segregating for downy mildew resistance,
  b) screening said population using a kit which detects at least one of the SNP markers listed in Table 4, and,
  c) identifying a plant comprising said at least one SNP marker selected in the list of Table 4.

In a further embodiment, the invention provides a method for identifying a squash source of downy mildew resistance trait on chromosome 9, comprising:
  a) providing a squash accession or a plurality of squash accessions, b) screening said squash accession or plurality of squash accessions using a kit which detects at least one of the SNP markers listed in Table 4, and, c) identifying a wild squash accession comprising said at least one SNP marker selected in the list of Table 4.

In yet another embodiment, the invention relates to the use of at least one SNP marker amplified from the genome of a squash plant according to any of the preceding embodiments, preferably from the genome of *Cucurbita pepo* plant 21SQN100201, representative seed of which is deposited under ATCC Accession No. PTA-127157, or a progeny or an ancestor thereof, wherein said SNP marker is identified using one of the SNP markers listed in Table 4 and wherein said SNP marker is indicative of the presence of the downy mildew resistance trait in a squash plant, to identify a squash plant that comprises and exhibits the downy mildew resistance trait.

In a further embodiment, the invention relates to a method for assessing the genotype of a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant, exhibiting resistance to downy mildew, said method comprising the steps of:

a) providing a sample from said plant, and, b) detecting in said sample a QTL locus located on chromosome 9 and associated with said downy mildew resistance, said QTL locus being flanked by SNP markers 1 and 8, and at least one of the following SNP markers:

i) a G genotype in the heterozygous or homozygous state for SNP marker 1 at a position corresponding to position 36 in SEQ ID NO: 1;

ii) a G genotype in the heterozygous or homozygous state for SNP marker 2 at a position corresponding to position 36 in SEQ ID NO: 2;

iii) a G genotype in the heterozygous or homozygous state for SNP marker 3 at a position corresponding to position 36 in SEQ ID NO: 3; iv) an A genotype in the heterozygous or homozygous state for SNP marker 4 at a position corresponding to position 36 in SEQ ID NO: 4;

v) an A genotype in the heterozygous or homozygous state for SNP marker 5 at a position corresponding to position 36 in SEQ ID NO: 5;

vi) an A genotype in the heterozygous or homozygous state for SNP marker 6 at a position corresponding to position 36 in SEQ ID NO: 6;

vii) an A genotype in the heterozygous or homozygous state for SNP marker 7 at a position corresponding to position 36 in SEQ ID NO: 7;

viii) an A genotype in the heterozygous or homozygous state for SNP marker 8 at a position corresponding to position 36 in SEQ ID NO: 8; and/or ix) any other DNA marker associated with said QTL locus flanked by SNP markers 1 and 8.

In a further embodiment, the invention relates to a method of identifying in a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant, an introgressed sequence associated with an increased resistance to downy mildew, said method comprising the step of detecting in said plant an allele of at least one DNA marker that is genetically linked to a QTL locus associated with said increased resistance to downy mildew, wherein said allele maps within 10 cM, preferably within 5 cM of said QTL locus located on chromosome 9 in a genomic region flanked by SNP markers 1 and 8.

In a further embodiment, the invention relates to the method of the preceding embodiment, wherein said QTL locus can be identified by at least one of the following SNP markers a) a G genotype in the heterozygous or homozygous state for SNP marker 1 at a position corresponding to position 36 in SEQ ID NO: 1;

b) a G genotype in the heterozygous or homozygous state for SNP marker 2 at a position corresponding to position 36 in SEQ ID NO: 2;

c) a G genotype in the heterozygous or homozygous state for SNP marker 3 at a position corresponding to position 36 in SEQ ID NO: 3;

d) an A genotype in the heterozygous or homozygous state for SNP marker 4 at a position corresponding to position 36 in SEQ ID NO: 4;

e) an A genotype in the heterozygous or homozygous state for SNP marker 5 at a position corresponding to position 36 in SEQ ID NO: 5;

f) an A genotype in the heterozygous or homozygous state for SNP marker 6 at a position corresponding to position 36 in SEQ ID NO: 6;

g) an A genotype in the heterozygous or homozygous state for SNP marker 7 at a position corresponding to position 36 in SEQ ID NO: 7; and/or, h) an A genotype in the heterozygous or homozygous state for SNP marker 8 at a position corresponding to position 36 in SEQ ID NO: 8.

In a further embodiment, the invention relates to the method of the preceding embodiment, wherein said method further comprises the step of selecting a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant comprising said introgressed sequence.

In a further embodiment, the invention relates to a method of identifying a cultivated squash plant, preferably a cultivated *C. pepo* plant, more preferably a cultivated *C. pepo* subsp. *pepo* plant, even more preferably a cultivated *C. pepo* subsp. *pepo* var. *cylindrica* plant, exhibiting increased resistance to downy mildew by identifying a QTL associated with said increased resistance to downy mildew, the method comprising the steps of:

a) detecting at least one DNA marker from a squash plant, which DNA marker is linked to a chromosomal interval associated with increased resistance to downy mildew, wherein said chromosomal interval is flanked on each side by SNP markers having at least 80% sequence identity to SEQ ID NOs: 1 and 8; and b) identifying said squash plant comprising said at least one DNA marker.

Uses.

The present invention also relates to the use of downy mildew resistance-propagating material obtainable from a squash plant according to any of the preceding embodiments for growing a squash plant to produce downy mildew resistant squash plants wherein said downy mildew resistance may be assessed in a standard assay, particularly an assay as described in Example 2 below.

The present invention also relates to the use of downy mildew resistance propagating material obtainable from a squash plant according to any of the preceding embodiments for producing squash fruits.

In another embodiment the invention relates to the use a cultivated squash plant, plant part or seed, more preferably a cultivated *C. pepo* subsp. *pepo* var. cylindrical plant, plant part or seed according to any of the preceding embodiments for growing a plant and producing and harvesting crops and/or fruits.

In another embodiment the invention relates to the use of a cultivated squash plant, more preferably a cultivated *C. pepo* subsp. *pepo* var. cylindrical plant, according to any of the preceding embodiments for producing fruits for the fresh market or for food processing.

In another embodiment the invention relates to the use of a cultivated squash plant, plant part or seed, preferably a cultivated *C. pepo* subsp. *pepo* var. cylindrical plant, plant part or seed according to any of preceding embodiments, wherein said cultivated squash plant, plant part or seed, preferably the cultivated *C. pepo* subsp. *pepo* var. cylindrical plant, plant part or seed is of *Cucurbita pepo* plant 21SQN100201, representative seed of which is deposited under ATCC Accession No. PTA-127157, or a progeny or an ancestor thereof.

In a further embodiment the invention relates to the use of a cultivated squash plant, plant part or seed, more preferably a cultivated *C. pepo* subsp. *pepo* var. cylindrical plant, plant part or seed according to any of the preceding embodiments to sow a field, a greenhouse, or a plastic house.

In a further embodiment the invention relates to the use of a squash plant according to any of the preceding embodiments to confer the increased downy mildew resistance trait to a squash plant lacking said trait. The invention further relates to the use of a squash plant according to any of the preceding embodiments to introgress an increased downy mildew resistance trait into a squash plant lacking said trait.

In a further embodiment the invention relates to the use of any of SEQ ID NOs 1-8 for screening a population of squash plants for the presence of a QTL locus located on chromosome 9 and associated with an increased downy mildew resistance.

In a further embodiment the invention relates to the use of SEQ ID NO 3 for screening a population of squash plants for the presence of a QTL locus located on chromosome 9 and associated with an increased downy mildew resistance.

Based on the description of the present invention, the skilled person who is in possession of *Cucurbita pepo* plant 21SQN100201, representative seed of which is deposited under ATCC Accession No. PTA-127157, or a progeny thereof, comprising said introgressed genetic sequence, as described herein, has no difficulty to transfer the said introgressed genetic sequence of the present invention to other squash plants of various types using breeding techniques well-known in the art with the support of SNP markers herein disclosed.

Seed Deposit Details

Applicant has made a deposit of 625 seeds of *Cucurbita pepo* plant 21SQN100201 with ATCC (American Type Culture Collection (ATCC), 10801 University Boulevard, Manassas, Va. 20110 USA) on 29 Oct. 2021 under ATCC Accession No. PTA-127157. Applicant elects for the expert solution and requests that the deposited material be released only to an Expert according to Rule 32(1) EPC or corresponding laws and rules of other countries or treaties (Expert Witness clause), until the mention of the grant of the patent publishes, or from 20 years from the date of filing if the application is refused, withdrawn or deemed to be withdrawn.

*Cucurbita pepo* hybrid plant 21SQN100201 is heterozygous for the downy mildew resistance QTL on chromosome 9, i.e., *Cucurbita pepo* plant 21SQN100201 comprises one copy of the introgressed sequence on chromosome 9 that is associated with increased downy mildew resistance.

EXAMPLES

Example 1: Germplasm and Population Development

A precocious yellow *Cucurbita pepo* subsp. *ovifera* var. *recticollis* squash line, 06SQN001028, was identified in our internal breeding germplasm as exhibiting increased downy mildew resistance and was therefore used as a source for downy mildew trait introgression into green zucchini and grey zucchini squash types.

A F1 population resulting from a cross between the precocious yellow squash line 06SQN001028 and a grey zucchini breeding line 07SQN200077 was self-pollinated four times via single seed descent to obtain 235 F5 Recombinant Inbred Lines (RIL). Lines from the F5 RILs were screened for downy mildew resistance in a field assessed according to the phenotypic evaluation described in Example 2A-C below. A QTL associated with increased downy mildew resistance was identified in this F5 RILs (see Examples 3 to 5).

Phenotypic backcrossing through disease screening was thereafter used to track the introgression of this resistance into cultivated, commercial acceptable, squash lines possessing different genetic backgrounds: green zucchini and grey zucchini. After sufficient backcrossing to introgress the downy mildew resistance into these lines and recover desirable agronomic and horticultural traits, self-progeny plants were generated to produce backcross families homozygous at the QTL locus. Converted breeding lines and their corresponding hybrids were screened for downy mildew resistance in a field assessed according to the phenotypic evaluation described in Example 2A-C below.

One squash plant derived from phenotypic backcrossing, 21SQN100201, was retained and deposited at ATCC on 29 Oct. 2021 under ATCC Accession No. PTA-127157. Squash plant 21SQN100201 is heterozygous for the downy mildew resistance trait, i.e., it comprises one copy of the downy mildew resistance-conferring introgressed sequence from the precocious yellow squash breeding line 06SQN001028.

Example 2: Protocols

Example 2A. *Pseudoperonospora cubensis* Isolate

*Pseudoperonospora cubensis* (*P. cubensis*) isolate culture stocks were maintained on frozen leaf tissue for long term storage. *P. cubensis* was cultured by washing spores off stored leaf tissue in distilled water. Using a haemocytometer, a spore concentration of $1 \times 10^4$ sporangia/ml water was inoculated onto susceptible seedling flats at the 2-3 true leaf stage for inoculum increase. Flats were maintained in growth chamber at 75 F-85 F for 7-10 days to increase inoculum. Symptomatic leaves were then harvested from the seedlings and washed in distilled water to remove spores. Spores were quantified using a haemocytometer. The spore concentration was adjusted to $1 \times 10^4$ sporangia/ml with sterile distilled H2O.

Example 28. Preparation and Inoculation of Plants

The 235 F5 RILs were evaluated for downy mildew resistance using an artificial inoculation method. Thirty-six seeds of each line were directly sown in a field in Naples, Fla. Thirty-six seeds from each line were divided into three replicates of twelve seeds. Replicates were distributed into a randomized complete block design on 0.5 acres of land. In addition, six seeds each of susceptible control plants 15SQN200046 and 08SQN000001 were sown in each field block to use as checks. Plants were inoculated 21-28 days (3-4 true leaves) after planting using *P. cubensis* inoculum prepared as described above. Five ml spore suspension is sprayed onto each plant two to three times one week apart.

The converted lines and their corresponding F1 hybrids were evaluated for downy mildew resistance using an artificial inoculation method. Seventy-two seeds of each material were directly sown in a field in Naples, Fla. Seventy-two seeds from each line were divided into six replicates of twelve seeds. Replicates were distributed into a randomized complete block design on 0.5 acres of land. In addition, seventy-two seeds each of susceptible control plants 15SQN200046 and 08SQN000001 and were sown in each field block to use as checks. Plants were inoculated 21-28 days (3-4 true leaves) after planting using *P. cubensis* inoculum prepared as described above. One hundred ml spore suspension is sprayed onto each plant two to three times one week apart.

Example 2C. Scoring of Downy Mildew Resistance

The first symptoms such as yellow brown lesions on the leaves appeared 10-14 days post-inoculation (dpi). Plants were monitored and symptoms were assessed at 14, 21 and 28 dpi. Plants were scored in a quantitative scale as described below and illustrated in FIG. 1.
Rating Symptoms
9 Healthy plants with no symptoms.
8 Lesion area covers 1%-5% of total leaf canopy.
7 Lesion area covers 5%-15% of total leaf canopy.
6 Lesion area covers 16%-30% of total leaf canopy.
5 Lesion area covers 31%-45% of total leaf canopy.
4 Lesion area covers 46%-60% of total leaf canopy.
3 Lesion area covers 61%-75% of total leaf canopy.
2 Lesion area covers 76%-90% of total leaf canopy.
1 Lesion area covers 91%-100% of total leaf canopy.

All plants were scored on the semi-quantitative rating scale (1-9) above. The disease scores were calculated for each line using adjusted mean by line with individual plant scoring using the following calculation:

$$Score=((R*9)+(S*8)+(T*7)+(U*6)+(V*5)+(W*4)+(X*3)+(Y*2)+(Z*1))/R+S+T+U+V+W+X+Y+Z;$$

wherein
R=number of plants with a score equal to 9;
S=number of plants with a score equal to 8;
T=number of plants with a score equal to 7;
U=number of plants with a score equal to 6;
V=number of plants with a score equal to 5;
W=number of plants with a score equal to 4;
X=number of plants with a score equal to 3;
Y=number of plants with a score equal to 2; and
Z=number of plants with a score equal to 1.

Example 2D. Method of Identifying the QTL and Corresponding Introgressed Sequence Underlying the Downy Mildew Increased Resistance Trait For QTL discovery, bulks of 6 plants from the 235 RIL families of the "precocious yellow squash line 06SQN001028×grey zucchini breeding line 07SQN200077" population were genotyped with 2079 genetic markers spanning the genome and a genetic map was calculated. These plants were grown and evaluated for downy mildew as described in Example 2A-C above.

The QTL detection was performed using the R/qtl package in the R statistical framework. First, the function 'calc.genoprob' was used to calculate the genotype probabilities (step 1 cM). Haley-Knott regression was performed to provide an approximation of the results of standard interval mapping. Then, the function 'stepwiseqtl' was invoked, which provides a fully automated model selection forward/backward algorithm. LOD threshold for main effect was determine by 10,000 permutations. This algorithm considers different possible interactions (e.g., epistasis). The function 'refineqtl' was used to refine the locations of QTL in the context of a multiple QTL model (maximum likelihood estimates). The function 'fitqtl' was used to fit a defined QTL model and obtain estimates of QTL effects.

Example 3: Identification of One Qtl Associated with Increased Downy Mildew Resistance One QTL was identified based on the downy mildew resistance phenotypes from the RIL population. Table 1 shows the chromosomal location, the effect of the QTL measured as LOD score, and the percentage of variation explained by the QTL on chromosome 9 for downy mildew resistance. The QTL showed a semi-dominant effect in the RIL population.

TABLE 1

| Significant QTL associated with downy mildew resistance. | | | |
| --- | --- | --- | --- |
| Chromosome | LOD | % var | Pvalue (F) |
| 9 | 13.2 | 16.9 | 1.21e−14*** |

"LOD" = log likelihood score "% var" = percent phenotypic variation explained by the QTL,
"Pvalue (F)" = the probability of the QTL detected due to random chance by F test.

Example 4: Introgression of the Downy Mildew Resistance Conferring Sequence into Commercial Background The *Cucurbita pepo* subsp. *pepo* var. *cylindrica* squash plants are of open, upright, plant type with cylindrical fruit green in color, whereas *Cucurbita pepo* subsp. *ovifera* var. *recticollis* squash plants have compact, semierect plant type with bulbish shaped fruit precocious yellow in color. The genetic sequence associated with increased resistance to downy mildew present in *Cucurbita pepo* subsp. *ovifera* var. *recticollis* squash plants was introgressed into Green zucchini line 09SQN001932 and Grey zucchini line 07SQN200077 by selecting resistant plants after artificial test described in Example 2 and backcrossing them to the respective squash types.

The introgressed lines highlighted a similar phenotype to that of the recurrent parent in terms of open, upright plant type with cylindrical or teardrop shaped fruit green in color while comprising the favourable introgressed sequence for increased downy mildew resistance. The phenotyping results, along with the results of testing for the presence or absence of representative markers in QTL9, are summarized in Table 2 below for the 09SQN001932 and 07SQN200077 backgrounds.

TABLE 2

Presence or absence of flanking and characterizing SNP markers for QTL9 and corresponding downy mildew phenotypes.

| | | Line | QTL9 region | | | |
|---|---|---|---|---|---|---|
| | Material ID and type | resistance test | 1/ AXQ1390 | 3/ AXQ1983 | 5/ AXQ17259 | 8/ AXQ1511 |
| 1. | 15SQN200046: Susceptible control | 4 | 0 | 0 | 0 | 0 |
| 2. | 06SQN001028, 08SQN000001: Original donor | 8 | 1 | 1 | 1 | 1 |
| 3. | 09SQN001932: Green Zucchini Recurrent parent | 5 | 0 | 0 | 0 | 0 |
| 4. | 18SQN002491, 20SQN200727: Green Zucchini Converted line | 6 | 1 | 1 | 1 | 1 |
| 5. | 19SQN001866, 21SQN100201: Green Zucchini pre-commercial hybrid/Seed deposit | 7 | H | H | H | H |
| 6. | 07SQN200077: Grey Zucchini Recurrent parent | 2.5 | 0 | 0 | 0 | 0 |
| 7. | 15SQN000553: Grey Zucchini Converted line | 6 | 1 | 1 | 1 | 1 |

Figure 2:
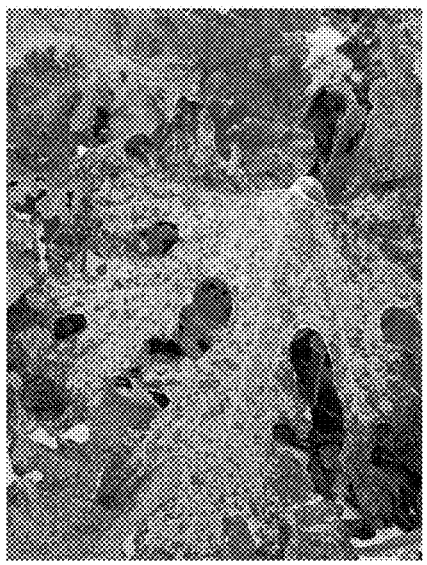
FIG. 2 shows the results of a downy mildew pathology assay carried out with a susceptible check (a) and a squash plant according to the invention, namely pre-commercial green zucchini hybrid plant 21SQN100201 (b).
Figure 2:
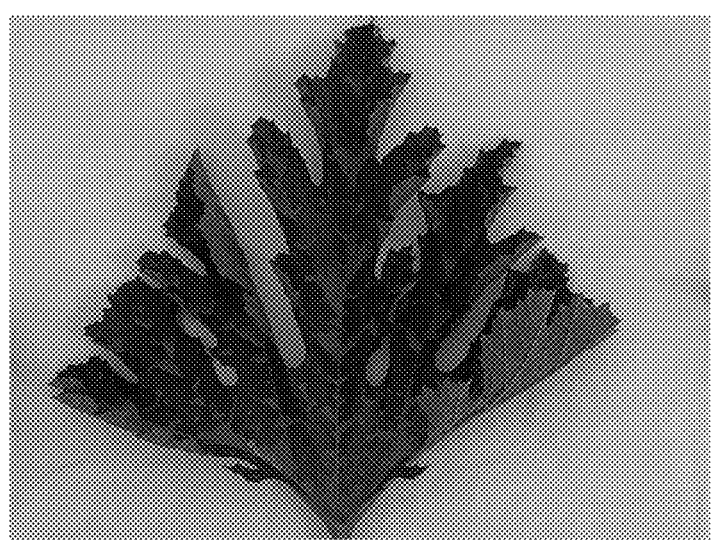

Existing susceptible control plant (plant 1) as well as recurrent parents in green zucchini and grey zucchini squash types (plant 3 and 6 respectively) exhibit severely susceptible or moderately susceptible phenotypes. Converted lines in both green zucchini and grey zucchini squash types (e.g., plants 4 and 7) comprising the SNP markers spanning and comprising the introgressed sequence underlying QTL9 exhibited an increased downy mildew resistance compared with their non-converted recurrent versions, achieving a disease score of at least 6. Furthermore, one pre-commercial hybrid (plant 5), also exhibited increased downy mildew resistance, even though it comprises only one copy of QTL9 (see FIG. 2).

Within this region, eight SNP markers, AXQ1390, AXQ12041, AXQ1983, AXQ13319, AXQ17259, AXQ4796, AXQ18568 and AXQ1511 within the QTL interval showed specificity for the selection of donor resistant allele from the resistance donor, and from them, SNP marker AXQ1983 is the most closely linked to the resistance.

Table 3 shows both genetic and physical positions of the QTL on chromosome 9 as well as the positions of the eight SNP markers tightly linked with the QTL. Physical positions are provided with reference to an internal genome assembly of chromosome 9 and the public genome assembly of Cp4.1 LG09 (Montero-Pau et al., 2018).

TABLE 3

Genetic map of the QTL on chromosome 9

| SNP ID | SNP Locus | Position (cM) | Physical position (bp; chromosome 9) | Physical position (bp; Cp4.1LG09) | Observation |
|---|---|---|---|---|---|
| 1 | AXQ1390 | 18.4 | 1 751 041 | 1713110 | SNP specific to R allele |
| 2 | AXQ12041 | | 1 851 800 | 1813930 | SNP specific to R allele |
| 3 | AXQ1983 | | 1 909 115 | 574 (Cp4.1_scaffold005972) | SNP specific to R allele |
| 4 | AXQ13319 | | 2 292 097 | 2206708 | SNP specific to R allele |
| 5 | AXQ17259 | | 2 527 216 | 2449634 | SNP specific to R allele |
| 6 | AXQ4796 | | 2 547 069 | 2471652 | SNP specific to R allele |
| 7 | AXQ18568 | | 2 561 697 | 2486280 | SNP specific to R allele |
| 8 | AXQ1511 | 27.9 | 2 582 083 | 2509209 | SNP specific to R allele |

Example 5: Sequence and SNP Marker Information for QTL9

The sequence information of Axiom markers 1 to 8 (AXQ1390, AXQ12041, AXQ1983, AXQ13319, AXQ17259, AXQ4796, AXQ18568, AXQ1511) is summarized in Table 4 below.

TABLE 4

| MARKER | 1/ AXQ1390 | 2/ AXQ12041 | 3/ AXQ1983 | 4/ AXQ13319 |
|---|---|---|---|---|
| Resistant Allele | G | G | G | A |
| Susceptible Allele | C | A | A | C |

TABLE 4-continued

| Target Sequence: SEQ ID NO. | 1 | 2 | 3 | 4 |
|---|---|---|---|---|
| SNP Position in Target SEQ: nt | 36 | 36 | 36 | 36 |

| MARKER | 5/ AXQ17259 | 6/ AXQ4796 | 7/ AXQ18568 | 8/ AXQ1511 |
|---|---|---|---|---|
| Resistant Allele | A | A | A | A |
| Susceptible Allele | C | G | G | C |
| Target Sequence: SEQ ID NO. | 5 | 6 | 7 | 8 |
| SNP Position in Target SEQ: nt | 36 | 36 | 36 | 36 |

As a matter of example, SNP marker 1 (AXQ1390) at position 1,751,041 bp and position 1,713,110 on chromosome 9 (based on internal genome assembly and public genome assembly, respectively) is characterized by a particular sequence polymorphism (resistant donor allele vs. susceptible allele) at position 36 of the target sequence of SEQ ID NO: 1.

BIBLIOGRAPHY

Food and Agriculture Organization of the United Nations, Statistics Division, FAOSTAT.
http://www.fao.org/faostat/en/#home Frost, 2015, Identifying and marketing quality open-pollinated and organic cucurbit seedstocks for Virginia, Final report for FS13-273.
https://projects.sare.org/project-reports/fs13-273/

Montero-Pau et al., 2018, De novo assembly of the zucchini genome reveals a whole-genome duplication associated with the origin of the *Cucurbita* genus, Plant Biotechnol. J. 16(6), p 1161-1171.

Newark et al., 2019, Management of cucurbit downy mildew in Florida, University of Florida IFAS Extension PP325.
https://edis.ifas.ufl.edu/pdf/PP/PP32500.pdf United States Department of Agriculture, National Agricultural Statistics Service, Vegetables 2019 Summary.
https://www.nass.usda.gov/Publications/Todays_Reports/reports/vegean20.pdf

The invention claimed is:

1. A cultivated squash plant resistant to downy mildew infection, comprising in its genome an introgressed sequence from *Cucurbita pepo* subsp. *ovifera* var. *recticollis* which confers resistance to downy mildew, wherein said introgressed sequence is located on chromosome 9 and comprises at least one of the following SNP markers:
   a) a G genotype in the heterozygous or homozygous state for SNP marker 1 at a position corresponding to position 36 in SEQ ID NO: 1;
   b) a G genotype in the heterozygous or homozygous state for SNP marker 2 at a position corresponding to position 36 in SEQ ID NO: 2;
   c) a G genotype in the heterozygous or homozygous state for SNP marker 3 at a position corresponding to position 36 in SEQ ID NO: 3;
   d) an A genotype in the heterozygous or homozygous state for SNP marker 4 at a position corresponding to position 36 in SEQ ID NO: 4;
   e) an A genotype in the heterozygous or homozygous state for SNP marker 5 at a position corresponding to position 36 in SEQ ID NO: 5;
   f) an A genotype in the heterozygous or homozygous state for SNP marker 6 at a position corresponding to position 36 in SEQ ID NO: 6;
   g) an A genotype in the heterozygous or homozygous state for SNP marker 7 at a position corresponding to position 36 in SEQ ID NO: 7; and,
   h) an A genotype in the heterozygous or homozygous state for SNP marker 8 at a position corresponding to position 36 in SEQ ID NO: 8;
wherein said introgressed sequence is comprised in *Cucurbita pepo* plant 21SQN100201, representative seed of which is deposited under ATCC Accession No. PTA-127157.

2. The plant according to claim 1, wherein said cultivated squash plant is a cultivated *C. pepo* plant and the introgressed sequence comprises at least one of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

3. The plant according to claim 1, wherein said plant is homozygous for said at least one SNP marker.

4. The plant of claim 1 wherein said plant is obtained by crossing *Cucurbita pepo* plant 21SQN100201, representative seed of which is deposited under ATCC Accession No.

PTA-127157, with a squash plant that does not contain said downy mildew resistance-conferring introgressed sequence.

5. The plant of claim 1 wherein said plant is an inbred, a dihaploid, a diploid, or a hybrid plant.

6. A plant of *Cucurbita pepo* plant 21SQN100201, representative seed of which is deposited under ATCC Accession No. PTA-127157.

7. A plant part of a plant according to claim 1.

8. A seed that produces a plant or a plant part according claim 1.

9. A method for producing a cultivated squash plant resistant to downy mildew infection comprising the steps of
   a) crossing a plant according to claim 1 with a cultivated squash plant lacking said downy mildew resistance-conferring introgressed sequence;
   b) selecting a progeny plant comprising said introgressed sequence located on chromosome 9 conferring resistance to downy mildew, said selecting step comprising detecting at least one of the following SNP markers:
      i) a G genotype in the heterozygous or homozygous state for SNP marker 1 at a position corresponding to position 36 in SEQ ID NO: 1;
      ii) a G genotype in the heterozygous or homozygous state for SNP marker 2 at a position corresponding to position 36 in SEQ ID NO: 2;
      iii) a G genotype in the heterozygous or homozygous state for SNP marker 3 at a position corresponding to position 36 in SEQ ID NO: 3;
      iv) an A genotype in the heterozygous or homozygous state for SNP marker 4 at a position corresponding to position 36 in SEQ ID NO: 4;
      v) an A genotype in the heterozygous or homozygous state for SNP marker 5 at a position corresponding to position 36 in SEQ ID NO: 5;
      vi) an A genotype in the heterozygous or homozygous state for SNP marker 6 at a position corresponding to position 36 in SEQ ID NO: 6;
      vii) an A genotype in the heterozygous or homozygous state for SNP marker 7 at a position corresponding to position 36 in SEQ ID NO: 7; and,
      viii) an A genotype in the heterozygous or homozygous state for SNP marker 8 at a position corresponding to position 36 in SEQ ID NO: 8;
   thereby producing a plant with enhanced resistance to downy mildew.

10. The method according to claim 9, wherein the method further comprises:
    c) selfing the selected progeny or crossing the selected progeny with another squash plant to produce further progeny.

11. The method according to claim 10, wherein further progeny is selected and selfed/crossed for 2 to 10 more generations.

12. The method according to claim 9 wherein the plant of step a) is *Cucurbita pepo* plant 21SQN100201, representative seed of which is deposited under ATCC Accession No. PTA-127157.

13. A method for producing a F1 squash plant exhibiting resistance to downy mildew, the method comprising crossing an inbred squash plant, which is a plant according to claim 1, with a different inbred squash plant to produce F1 hybrid progeny.

14. A method for identifying a cultivated squash plant resistant to downy mildew infection and having at least one copy of said downy mildew resistance-conferring introgressed sequence, said method comprising the step of detecting at least one of the following SNP markers:
    a) a G genotype in the heterozygous or homozygous state for SNP marker 1 at a position corresponding to position 36 in SEQ ID NO: 1;
    b) a G genotype in the heterozygous or homozygous state for SNP marker 2 at a position corresponding to position 36 in SEQ ID NO: 2;
    c) a G genotype in the heterozygous or homozygous state for SNP marker 3 at a position corresponding to position 36 in SEQ ID NO: 3;
    d) an A genotype in the heterozygous or homozygous state for SNP marker 4 at a position corresponding to position 36 in SEQ ID NO: 4;
    e) an A genotype in the heterozygous or homozygous state for SNP marker 5 at a position corresponding to position 36 in SEQ ID NO: 5;
    f) an A genotype in the heterozygous or homozygous state for SNP marker 6 at a position corresponding to position 36 in SEQ ID NO: 6;
    g) an A genotype in the heterozygous or homozygous state for SNP marker 7 at a position corresponding to position 36 in SEQ ID NO: 7; and,
    h) an A genotype in the heterozygous or homozygous state for SNP marker 8 at a position corresponding to position 36 in SEQ ID NO: 8;
thereby identifying a squash plant exhibiting resistance to downy mildew.

15. The method according to claim 14, wherein said method further comprises selecting a squash plant comprising said one or more SNP markers, and crossing the selected squash plant with a second squash plant to produce progeny squash plants that comprise at least one of said SNP markers and exhibits resistance to downy mildew.

16. A method of producing squash seed, the method comprising growing a squash plant from the seed of claim 8 and allowing the plant to produce further squash seed.

17. A method for assessing the genotype of a cultivated squash plant exhibiting resistance to downy mildew, said method comprising the steps of:
    a) providing a sample from said plant, and,
    b) detecting in said sample a QTL locus located on chromosome 9 and associated with said downy mildew resistance, said QTL locus being flanked by SNP markers 1 and 8, and at least one of the following SNP markers:
       i) a G genotype in the heterozygous or homozygous state for SNP marker 1 at a position corresponding to position 36 in SEQ ID NO: 1;
       ii) a G genotype in the heterozygous or homozygous state for SNP marker 2 at a position corresponding to position 36 in SEQ ID NO: 2;
       iii) a G genotype in the heterozygous or homozygous state for SNP marker 3 at a position corresponding to position 36 in SEQ ID NO: 3;
       iv) an A genotype in the heterozygous or homozygous state for SNP marker 4 at a position corresponding to position 36 in SEQ ID NO: 4;
       v) an A genotype in the heterozygous or homozygous state for SNP marker 5 at a position corresponding to position 36 in SEQ ID NO: 5;
       vi) an A genotype in the heterozygous or homozygous state for SNP marker 6 at a position corresponding to position 36 in SEQ ID NO: 6;
       vii) an A genotype in the heterozygous or homozygous state for SNP marker 7 at a position corresponding to position 36 in SEQ ID NO: 7;

viii) an A genotype in the heterozygous or homozygous state for SNP marker 8 at a position corresponding to position 36 in SEQ ID NO: 8; and, ix) any other SNP marker associated with said QTL locus flanked by SNP markers 1 and 8.

18. The plant of claim 1 wherein said plant is a cultivated *Cucurbita pepo* subsp. *pepo* var. *cylindrica* plant.

\* \* \* \* \*